(12) United States Patent
Maxfield et al.

(10) Patent No.: US 8,583,258 B2
(45) Date of Patent: Nov. 12, 2013

(54) ELECTRODE LEAD IN PARTICULAR FOR USE WITH A MEDICAL IMPLANT

(75) Inventors: Michelle Maxfield, Berlin (DE); Ingo Weiss, Berlin (DE); Sonja Meine, Ilsede (DE)

(73) Assignee: Biotronik SE & Co. KG, Berlin (DE)

( * ) Notice: Subject to any disclaimer, the term of this patent is extended or adjusted under 35 U.S.C. 154(b) by 197 days.

(21) Appl. No.: 13/083,581

(22) Filed: Apr. 10, 2011

(65) Prior Publication Data

US 2011/0276116 A1 Nov. 10, 2011

Related U.S. Application Data

(60) Provisional application No. 61/331,396, filed on May 5, 2010.

(51) Int. Cl.
*A61N 1/00* (2006.01)

(52) U.S. Cl.
USPC .......................................................... 607/116

(58) Field of Classification Search
USPC .......................................................... 607/116
See application file for complete search history.

(56) References Cited

U.S. PATENT DOCUMENTS

| | | | |
|---|---|---|---|
| 5,246,014 A | 9/1993 | Williams | |
| 7,363,090 B2 | 4/2008 | Halperin | |
| 7,702,387 B2 * | 4/2010 | Stevenson et al. | 607/2 |
| 2003/0139739 A1 | 7/2003 | Doscher | |
| 2007/0179582 A1 | 8/2007 | Marshall | |
| 2008/0046059 A1 | 2/2008 | Zarembo | |
| 2009/0149920 A1 | 6/2009 | Li | |
| 2009/0281592 A1 * | 11/2009 | Vase | 607/37 |

OTHER PUBLICATIONS

European Search Report dated Aug. 22, 2011 (6 pages).

* cited by examiner

*Primary Examiner* — Christopher D Koharski
*Assistant Examiner* — Philip Edwards
(74) *Attorney, Agent, or Firm* — Arc IP Law, PC; Joseph J. Mayo

(57) ABSTRACT

A flexible electrode lead in particular for use with a medical implant comprises, an elongated electrode body with a proximal and a distal end, at least one conductor leading from the proximal towards the distal end of the electrode lead, a first ring element at the distal end of the electrode lead connected to the conductor and being positioned coaxially in the lead electrode body a second ring element spaced distally of the first ring element and being positioned coaxially in the lead electrode body, a coil conductor between the first and second ring element, wherein the coil conductor is adapted to form an inductance which is in parallel circuitry with the capacitor to form a filter element in the conductor, and the first ring element, the coil conductor and the second ring element comprise a central feedthrough for a guidance element for the electrode lead.

14 Claims, 5 Drawing Sheets

ELECTRODE LEAD IN PARTICULAR FOR USE WITH A MEDICAL IMPLANT

This application claims the benefit of U.S. Provisional Patent Application 61/331,396, filed 5 May 2010, the specification of which is hereby incorporated herein by reference.

BACKGROUND OF THE INVENTION

1. Field of the Invention

The present disclosure refers to an electrode lead in particular for use with a medical implant.

2. Description of the Related Art

Electrode leads for such use are known in a wide variety of embodiments, e. g. cardiac pacemaker leads for sensing and/or pacing, or active leads for implantable defibrillators. A problem occurs with such electrode leads, when they are placed in strong dynamic magnetic fields, like is the case during magnetic resonance imaging or close to radio transmission stations. Due to electromagnetic interference (EMI), radio frequency (RF) energy is picked up by the electrode lead. This energy exits the electrode lead at an electrode pole, which is connected and/or connectable to the electrode lead, like a tip electrode of a pacemaker electrode lead. Due to the high frequency, the exiting energy causes a heating of the surrounding tissue or blood what in turn may destroy the surroundings of the electrode, such as living tissue. Within the cardiac environment, this can increase e.g., pacing thresholds of an electrode lead used as a pacemaker lead, in the worst case this heating may make the lead ineffective.

The aforesaid problems are broadly discussed in U.S. Pat. No. 7,363,090 B2 which discloses a basic solution concept for the problem of the energy induced in an electrode lead by RF energy during MRI, namely, integrating a band stop filter into each lead wire leading to a ring and/or tip electrode of an electrode lead of an active implantable medical device (AIMD). This band stop filter includes a capacitor in parallel with an inductor. The parallel capacitor and inductor are placed in series with the implantable lead wire of the AIMD, wherein values of capacitance and inductance are selected such that the band stop filter is resonant at a selected frequency. In a preferred embodiment of the known electrode lead with band stop filter, the latter is integrated into the tip and/or ring electrode for the active implantable medical device.

Such electrode leads used in practice, as they are produced and marketed by the applicant of U.S. Pat. No. 7,363,090 show filter constructions in which the capacitor and the inductor are hermetically sealed in a drum which forms a cylindrical stiff element of considerable dimensions. Due to the large and bulky housing of this known filter, the electrode lead equipped with this filter has an unacceptable stiff tip section which is problematic when introducing the electrode lead into a body vessel. Bulky long stiff regions in the tip section may cause perforation of the body vessel which is a serious incident when positioning the electrode lead.

A further disadvantage of the known electrode lead with band stop filter is the fact that the electrode lead does not dispose of a central continuous lumen for guiding the electrode lead over a guide wire or mandrel because of the bulky massive filter element.

BRIEF SUMMARY OF THE INVENTION

Based on the cited problem of the prior art electrode lead with a massive bulky L-C-filter element, it is a feature of the invention to improve such an electrode lead as to achieve as least as possible stiffening in the tip region and to provide for a central continuous lumen.

This is achieved by an electrode lead as described and claimed herein.

Accordingly, the electrode lead according to the invention basically uses known components of such electrode leads, namely, first and second ring elements at the distal end of the electrode lead, like they are used with known electrodes leads for ring or tip electrodes. Such ring elements are positioned coaxially in the lead electrode body and have coaxial, central lumens for a guide wire or the like. Further, the coil conductor between the first and second ring element accords to a usual wire coil used in medical implant electrode leads and, thus, also shows a central coaxial lumen for a guide wire or the like. Thus a part existing per se in a medical lead is used to incorporate an element of a high frequency filter.

According to a preferred embodiment of the invention, the first ring element is adapted to be a capacitor including an external capacitor sleeve and an internal capacitor sleeve which together form an electrical component having a capacitance value which is defined by the dimensions of the capacitor sleeves, their radial distance and the dielectric constant of the dielectric placed between the two capacitor sleeves. This capacitor forms one part of the filter element, whereas the coil conductor between the first and second ring element is adapted to form an inductance and, thus, realizes the second necessary component for a filter element blocking high frequency currents induced by RF signals of MRI systems. Nevertheless, due to the assembly of the filter element based on standardized components such as rings and coils which can be state of the art, the electrode lead according to one or more embodiments of the invention shows the same mechanical and long term stability characteristics as known electrode leads. Further on, the novel electrode lead according to one or more embodiments of the invention still has an inner lumen. Finally, albeit the implementation of a capacitor and an inductance of the filter element thinner electrode leads can be constructed, as the first ring element forming the capacitor and the coil conductor are geometrically placed in series, thus, not requiring extra space in radial direction. Although the overall length of the filter element might be quite long, it can be flexible due to the coil conductor forming the inductance resulting in a more flexible construction as compared to the known solutions with massive, bulky housed filter elements of the prior art.

According to a preferred embodiment, the external and internal capacitor sleeve of the capacitor are separated by a dielectric which is adapted to match the inductance of the coil conductor. Thus, the capacitor can be adjusted to show the specified filter performance to create a tank filter or a band stop filter etc. Preferably, the dielectric is a dielectric coating, which might be realized by using:

DLC (Diamond Like Carbon, amorphous carbon, SP2+ SP3 carbon, ta-C tetrahedral amorphous carbon, hybridized carbon), TiN (Titanium nitride), DLC doped with gold or other conductive/semiconductive substances, Parylene (poly-para-xylylenes, chemical vapour deposited poly(p-xylylene) polymers), Titanium Nitride (TiN), silicon carbide (Carborundum), titanium oxide, silicone coating (silane, MD360 medical fluid, linear PDMS, polydimethylsiloxane, Silglide, Raumedic Dispersion 2607), Teflon (polytetrafluoroethylene),
Silicon (quartz, silica),
polyurethane,
epoxy (polyurethane, acrylic, cyanoacrylate, polyester),
Kapton (Polyimide, PI, poly-oxydiphenylene-pyromellitimide),
PET (Polyethylene terephthalate),
Polyamide (PA, PA-6, PA-66),
high permittivity plastics (High K Polyurethane with epsilon of 5.2),
aluminium oxide ($Al_2O_3$,)
silicon dioxide ($SiO_2$),
coatings made from polymer/elastomer filled with dielectric fillers such as: Ceramics (e.g. Barium Titanate BaTiO3) or passivated (oxide layer) metal particles (aluminium, tungsten, tantalum, titanium or alike) or silica-coated metal particles,
alternating polymer/passivated metal layers, or
ceramics.

As to the integration of the capacitor, it is possible to accommodate same in a flexible insulation tube of the electrode lead. An alternative would be to separate the first ring element defining the capacitor from the electrode body by surrounding the ring element with the dielectric coating. Thus, the connector is fixed at a given longitudinal position within the electrode lead.

According to further preferred embodiments, the coil conductor realizing the inductance is made of a high conductive material or coated with same. By the specification of this high conductive material, the coil conductor can be matched to the capacitance of the capacitor to achieve a desired filter performance of the filter element.

To improve the stability of the filter performance, i. e. to avoid any changes in the inductance of the coil conductor, at least a partial length of the latter, is accommodated in a stiff portion of the electrode body. This means that the coil windings do not change their relative position, thus, leading to a constant inductance value compared to a flexible coil in which deforming the coil would lead to a variation in the inductance value.

In order to avoid a negative influence of the remaining flexible region of the coil conductor, a preferred embodiment provides for an addition lead wire which shunts the flexible coil windings.

To ensure a proper wiring of the filter element with the second ring element, a lead wire may be provided which extends through the coil conductor. Preferably, this additional lead wire may be coiled into the coil conductor, thus, saving space in the region of the inner diameter of the coil conductor.

According to another preferred embodiment, the first ring element implementing the capacitor may be surrounded by an external metallic ring surface which may be realized by a metal coating fixed to the capacitor via an insulating coating. This design helps to decouple high frequency electromagnetic energy generated by the RF frequency in MRI applications. By this additional dissipation of energy, the heating of the electrode (s) is further minimized.

According to another preferred embodiment, the inner capacitor sleeve of the first ring element may be realized by a coating, preferably of titanium.

Finally, another preferred embodiment refers to a structure of a first ring element which is comprised of two coaxially fitted standard ring parts, which, however, do not form a capacitor. This function is fulfilled by a separate capacitor, preferably a micro capacitor which is contacted to at least one of these ring parts. The advantage of this construction lies in the fact that as a capacitor a standard electronic component can be used. Further on, the whole structure of two ring parts and the capacitor can be assembled easier even using plastic ring parts.

BRIEF DESCRIPTION OF THE DRAWINGS

Further features, details and advantages of the invention are disclosed in the following description of preferred embodiments referring to the accompanying drawings, in which.

DETAILED DESCRIPTION OF THE INVENTION

Figure 1:
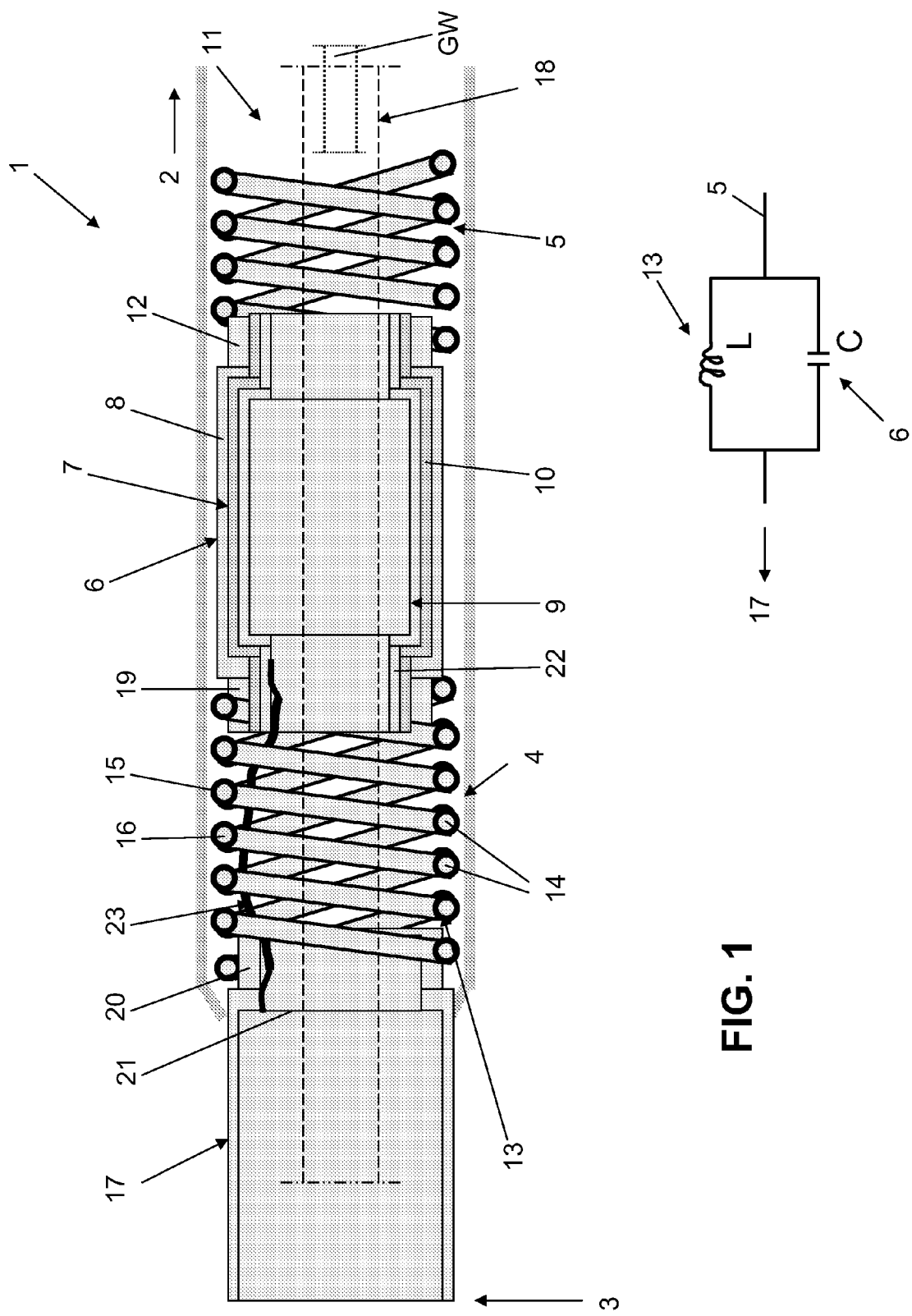
FIG. 1-5 show longitudinal sections of an electrode lead with filter elements in five different embodiments.

Referring to FIG. 1, the basic components of the electrode lead for use with a medical implant are described. The electrode lead includes an elongated electrode body 1 with a proximal and distal end 2, 3. The electrode body 1 is defined by an elongated flexible insulation tube 4 which is produced e. g. from a silicon tube. Within this insulation tube 4, a first coil conductor 5 connects the medical implant (not shown) at the proximal end of the electrode body 1 with the distal end 3. This coil conductor 5 is a standard lead coil used in such electrode leads and is made e. g. from medical steal material MP35N with an wire diameter of 0.12 mm.

At the distal end 3 of the electrode body 1, the coil conductor 5 terminates at a first ring element 6 which is positioned coaxially in the electrode body 1 of the electrode lead. This first ring element 6 implements a capacitor 7 which includes an external capacitor sleeve 8, an internal capacitor sleeve and a dielectric coating 10 placed between the external and internal capacitor sleeve 8, 9. As can be seen from FIG. 1, the first ring element 6 is covered by the insulation tube 4 and slidably positioned within the lumen 11 of the insulation tube 4. The external sleeve 8 is terminated by a proximal ring 12 which is contacted by the distal end of the coil conductor 5.

Following the first ring element 6 with capacitor 7, a second coil conductor 13 is placed within the lumen 11 of the insulation tube 4 in coaxial manner as concerns the longitudinal axis of the electrode body. The windings 14 of this coil conductor 13 are made of the high-conductive metal material or—as is depicted in FIG. 1—may have a special high-conductive surface coating 15 on the standard MP35N coil wire 16 to provide long term inductivity stability and a proper quality or performance value. The specification of the coil conductor 13 is adapted to match its inductance L to the capacitance C of the capacitor 7.

At the distal end 3, the electrode body 1 is terminated with a second ring element 17 which may be a tip electrode of the electrode lead. This ring element again is positioned coaxial to the longitudinal axis of the electrode body 1. All central openings of the first coil conductor 5, the first ring element 6, the second coil conductor 13 and the second ring element 17 form a central feed-through 18 depicted in dashed lines in FIG. 1. As is depicted in dotted lines, a guide wire GW can be fed through the feed-through 18 of the electrode lead.

As concerns electric circuitry, the second coil conductor 13 is electrically connected to the external capacitor sleeve 8 by means of a distal ring 19 on the external capacitor sleeve 8. The distal end of the coil conductor 13 is mechanically and electrically connected to a shoulder 20 at the proximal end of the ring element 17. The further electrical connection is provided for between the inner conductive surface 21 of the ring element 17 and a contact ring 22 fixed to the internal capacitor sleeve 9 of the capacitor 7. The connector is an insulated wire 23 which may be coiled or winded together with a coil conductor 13 to save space within the inner diameter of the coil conductor 13.

As can be seen in the sketch like wiring diagram inserted in FIG. 1, the first ring element 6 forming the capacitor 7 with the capacitance C and the coil conductor 13 providing for the conductance L are switched in parallel, both being connected to the coil conductor 5 arriving from the proximal end and to the ring element 17 at the distal end 3 of the electrode body.

Due to the known physical correlation between the inductance L and the capacitance C, the filter element formed by the capacitor 7 and the coil conductor 13 have a specified filter performance to block RF currents to enter the distal end of the electrode body and, especially, the ring element 17.

Due to the flexible character of the first and second coil conductors 5, 13, the overall flexibility of the electrode body especially in the region of the distal end is appropriate to achieve good bending properties facilitating the advancement of the electrode lead through a body vessel. However, this embodiment of FIG. 1 shows some restrictions as to the stability of the inductance L of the coil conductor 13, as the latter is flexible. Due to the varying geometry of the coil conductor, the inductance L varies when bending the coil conductor 13, thus, leading to a (small) mismatch of the inductance L as concerns the capacitance C. The embodiment of FIG. 2 avoids this problem.

Figure 2:
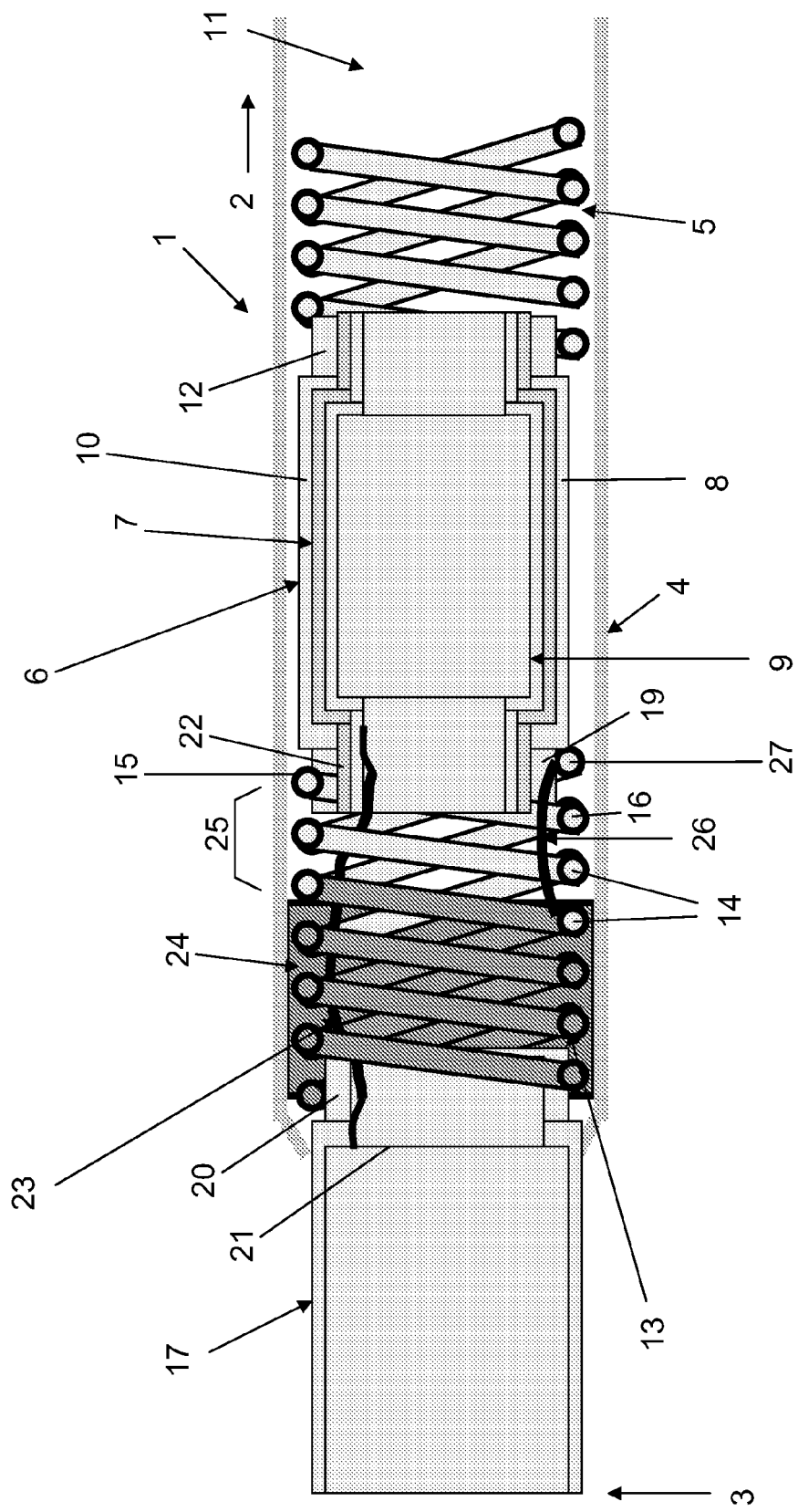

The embodiment shown in FIG. 2 in most of the parts is identical to the embodiment of FIG. 1. To avoid unnecessary repetitions, in the following only the differences are explained. Parts which are identical and have the same function as in the embodiment of FIG. 1 are indicated with identical reference numerals and need no further explanation here.

As is depicted in FIG. 2, a partial length of the coil conductor 13 starting from its distal end to about 60% of its length towards the proximal end 2 is accommodated in a stiff portion 24 depicted by bold lines in the insulation tube 4 of the electrode body 1. The remaining portion 25 of the coil conductor 13 is still positioned in the mechanically flexible region of the insulation tube 4 and, thus, can still be bended to facilitate the advancement of the electrode lead through a body vessel. Within the stiff portion 24, however, the coil wires 16 are stably positioned, thus, avoiding any variation in the proper inductance L. To avoid any negative influence of the flexible part of the coil conductor 13, the coil wires in this remaining portion 25 are bypassed by a shunt wire 26 connecting the rigid portion of the coil conductor 13 directly to the proximal end 27 of the coil conductor 13. The shunt wire is made of a high conductive metal material and has a negligible inductance. In case the shunt wire connection at one of its ends fails, the coil conductor 13 together with the capacitor 7 still serves as a backup DC connection for normal operation of the electrode lead.

Whereas FIG. 2 shows one stiff portion of the coil conductor, it is also possible to provide for several rigid portions of the coil conductor along its length with flexible portions in between. All stiff segments contribute to a desired inductance L matching to the capacitance C of capacitor 7.

Now turning to FIG. 3, again only the differences versa the embodiment of FIG. 1 are explained. Accordingly, the first ring element 6 implementing the capacitor 7 further comprises an external dielectric coating 28 which insulates the first ring element 6 at the external side. Thus the insulation tube 4 is interrupted at the location of the first ring element 6. The advantage of this embodiment lies in the fact that the dielectric coating 28 may be much thinner than the insulation tube 4. Thus the capacitor 7 can have a larger open inner diameter giving better access to e.g. guide wires to be inserted into the electrode lead. The drawing figure is a rough sketch which is not reflecting these thickness relations to scale.

Figure 3:
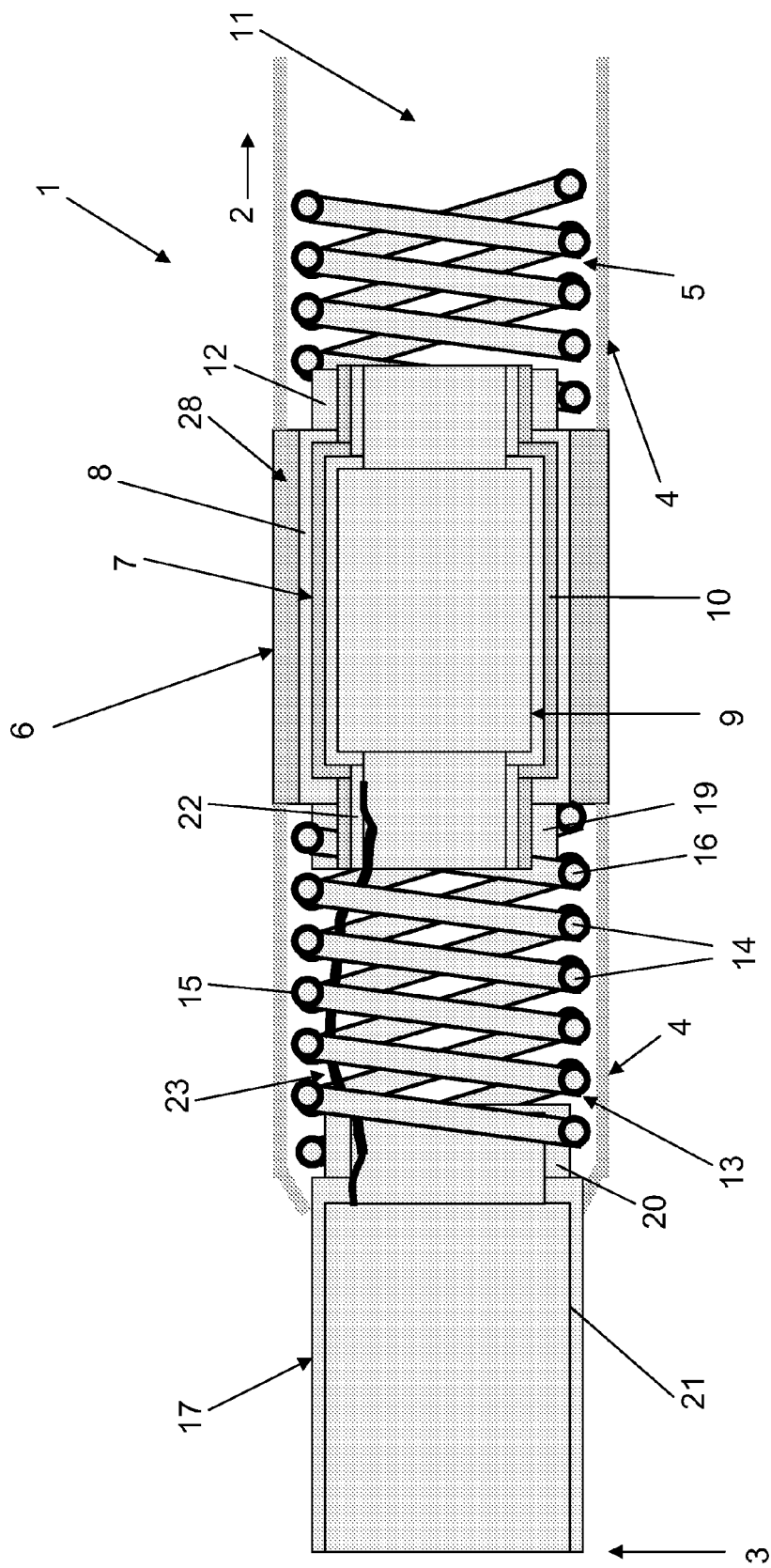

The remaining parts of the embodiment of FIG. 3 are identical to those of FIG. 1 and are thoroughly described above.

Figure 4:
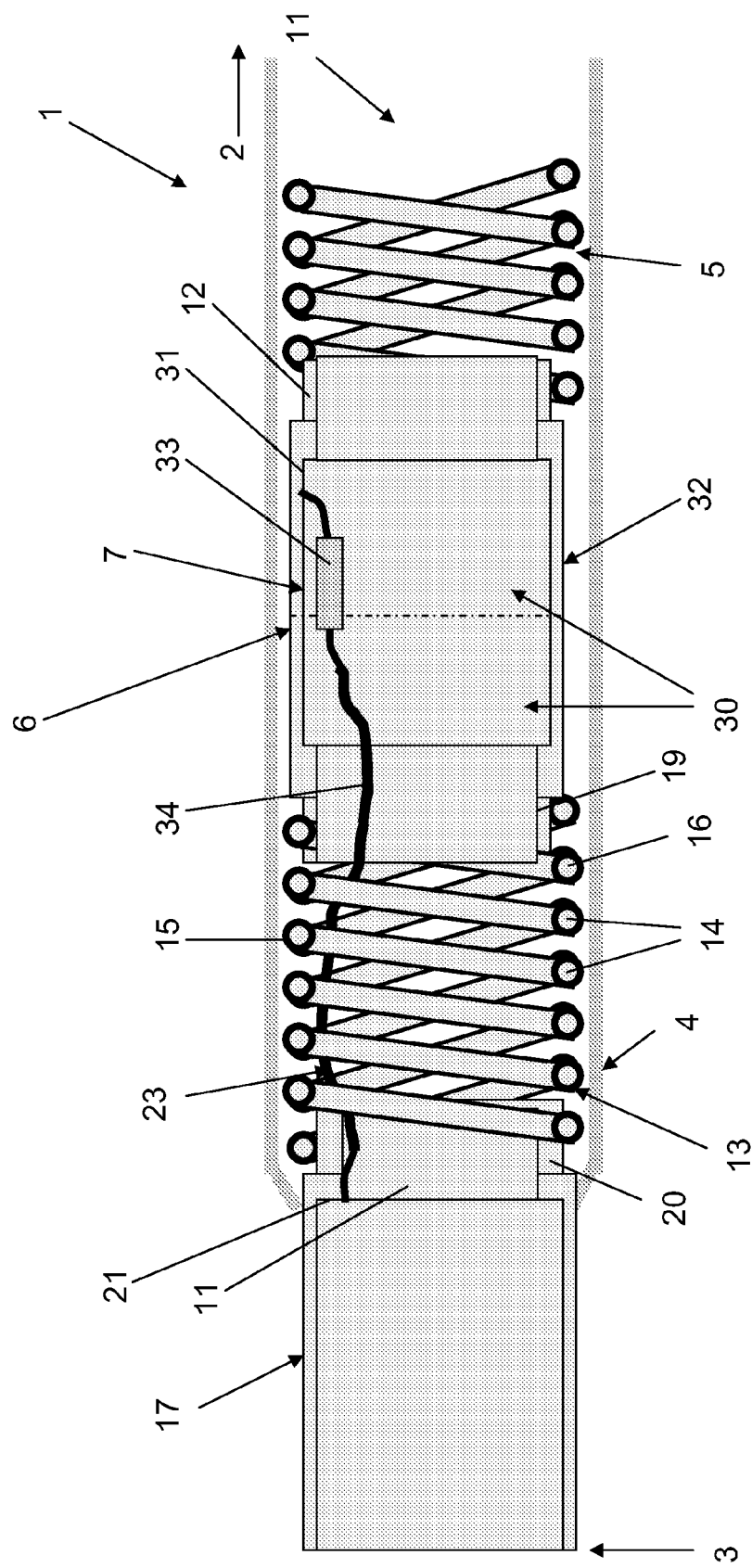

The embodiment according to FIG. 4 differs from the previous embodiments as concerns the construction of a first ring element 6 which is no capacitor in this case, but welded together from two standard rings 30 which have an inner conductive surface 31, e.g. made of plated titanium. Both rings 30 are welded together via a weld joint 32 depicted in dotted dashed lines in FIG. 4. As the capacitor a standard micro capacitor 33 is used, which is contacted to the conductive surface 31 of one of the standard rings 30 on the one hand and via a wire connection 34 to the second ring element 17 at the distal end 3 of the electrode body 1.

Aforesaid construction facilitates the manufacturing process, as the micro capacitor 33 may be contacted to the one ring 30 first. Afterwards both rings 30 are welded together. Thus the contacts of the capacitor 33 are also well protected.

Figure 5:
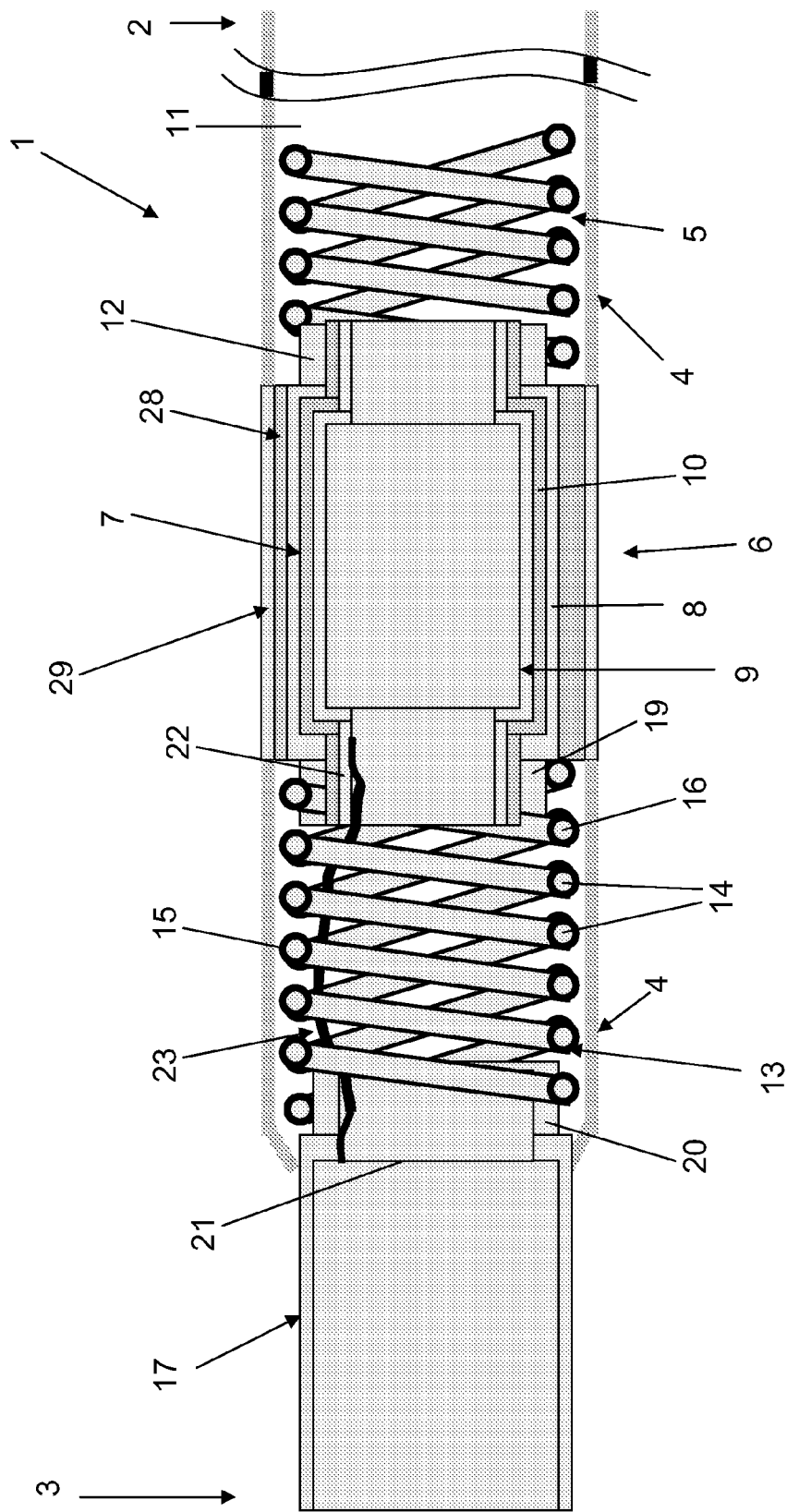

The last drawing FIG. 5 shows another version of the first ring element 6 which is a development of the embodiment of FIG. 3. In fact, the external dielectric coating 28 is further surrounded by an external metallic ring surface 29. This metal plating over the dielectric coating 28 serves the purpose of shielding the dielectric coating 28 from blood contact to ensure long term stability and biocompatibility. Boundary effects from the metal surface 29 or the ability to bring the surface in a flushing relationship to the neighbouring elements can also be a beneficial effect from the additional outer metal ring surface 29.

All dielectric materials and coatings cited above may be formed from materials like:
- DLC (Diamond Like Carbon, amorphous carbon, SP2+ SP3 carbon, ta-C tetrahedral amorphous carbon, hybridized carbon),
- TiN (Titanium nitride),
- DLC doped with gold or other conductive/semiconductive substances,
- Parylene (poly-para-xylylenes, chemical vapour deposited polyp-xylylene) polymers),
- Titanium Nitride (TiN),
- silicon carbide (Carborundum),
- titanium oxide,
- silicone coating (silane, MD360 medical fluid, linear PDMS, polydimethylsiloxane, Silglide, Raumedic Dispersion 2607),
- Teflon (polytetrafluoroethylene),
- Silicon (quartz, silica),
- polyurethane,
- epoxy (polyurethane, acrylic, cyanoacrylate, polyester),
- Kapton (Polyimide, PI, poly-oxydiphenylene-pyromellitimide),
- PET (Polyethylene terephthalate),
- Polyamide (PA, PA-6, PA-66),
- high permittivity plastics (High K Polyurethane with epsilon of 5.2),
- aluminium oxide ($Al_2O_3$,)
- silicon dioxide ($SiO_2$),
- coatings made from polymer/elastomer filled with dielectric fillers such as: Ceramics (e.g. Barium Titanate $BaTiO_3$) or passivated (oxide layer) metal particles (aluminium, tungsten, tantalum, titanium or alike) or silica-coated metal particles,
- alternating polymer/passivated metal layers, or
- ceramics.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention. In addition to the embodiments described herein other alternative embodiments may include some or all of the features disclosed therein.

REFERENCE NUMERAL LIST

1 Electrode body
2 Proximal end
3 Distal end
4 Insulation tube
5 Coil conductor
6 First ring element
7 Capacitor
8 External Capacitor sleeve
9 Internal Capacitor sleeve
10 Dielectric coating
11 Lumen
12 Proximal ring
13 Coil conductor
14 Winding
15 Surface coating
16 Coil wire
17 Ring element
18 Feedthrough
19 Distal ring
20 Shoulder
21 Inner conductive surface
22 Contact ring
23 insulated wire
24 Stiff portion
25 remaining portion
26 Shunt wire
27 Proximal end of coil conductor 13
28 Coating
29 Metallic ring surface
30 Standard ring
31 Conductive surface
32 Weld joint
33 Micro capacitor
34 Wire connection
GW Guide wire

What is claimed is:

1. An electrode lead for use with a medical implant comprising: an elongated electrode body with a proximal and a distal end having a longitudinal axis parallel to said elongated electrode body; at least one conductor that leads from the proximal end towards the distal end of the electrode lead; a first ring element located near the distal end of the electrode lead connected to the at least one conductor and positioned coaxially in the elongated electrode body wherein said first ring element comprises parallel cylinders that form a capacitor having a capacitance and wherein said parallel cylinders define capacitive surfaces that are parallel to said longitudinal axis; a second ring element at the distal end of the electrode lead and spaced distally at a longitudinal offset along said longitudinal axis from the first ring element and positioned coaxially in the elongated electrode body; a coil conductor electrically connected and located longitudinally along said longitudinal axis between the first and second ring element; wherein the coil conductor is configured to form an inductance which is in parallel circuitry with the first ring element to form a filter element in the at least one conductor and wherein at least a partial length of the coil conductor is accommodated in a stiff portion of the elongated electrode body configured to provide a stable inductance over said stiff portion of said elongated electrode body; and, wherein the first ring element, the coil conductor and the second ring element comprise a central feedthrough for a guidance element for the electrode lead.

2. The electrode lead according to claim 1, wherein the capacitor comprises an external capacitor sleeve and an internal capacitor sleeve.

3. The electrode lead according to claim 2, wherein the external and internal capacitor sleeve are separated by a dielectric which is configured to match the inductance of the coil conductor.

4. The electrode lead according to claim 3, wherein the dielectric is a dielectric coating.

5. The electrode lead according to claim 4, wherein the first ring element is surrounded by the dielectric coating that insulates the first ring element from the elongated electrode body.

6. The electrode lead according to claim 2, further comprising a flexible insulation tube wherein the capacitor is located in the flexible insulation tube of the electrode lead.

7. The electrode lead according to claim 2, further comprising a lead wire wherein an electrical connection between the second ring element and the capacitor realised by the first ring element is provided by the lead wire that extends through the coil conductor.

8. The electrode lead according to claim 2, wherein the capacitor of the first ring element is surrounded by an external metallic ring surface to decouple high frequency electromagnetic energy.

9. The electrode lead according to claim 8, wherein the external metallic ring surface comprises a metal coating fixed to the capacitor via an insulating coating.

10. The electrode lead according to claim 2, wherein the inner capacitor sleeve is a coating.

11. The electrode lead according to claim 2, wherein the inner capacitor sleeve is a titanium coating.

12. The electrode lead according to claim 1, wherein the coil conductor is made of or coated with a highly conductive material.

13. The electrode lead according to claim 12, further comprising a lead wire and wherein the coil windings in a remaining mechanically flexible region of the coil conductor are shunted by the lead wire to provide a redundant electrical connection in case of breakage of said coil windings.

14. The electrode lead according to claim 13, wherein the lead wire is coiled to the coil conductor.

* * * * *